(12) United States Patent
Colon et al.

(10) Patent No.: US 10,149,475 B2
(45) Date of Patent: *Dec. 11, 2018

(54) STABLE AQUEOUS DISPERSIONS OF BIOCIDES

(71) Applicant: Troy Technology II, Inc., Florham Park, NJ (US)

(72) Inventors: Ismael Colon, Denville, NJ (US); Richard S. Valpey, III, Rockaway, NJ (US); W. Brian Smith, Towaco, NJ (US)

(73) Assignee: Troy Technology II, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/674,474

(22) Filed: Aug. 10, 2017

(65) Prior Publication Data

US 2018/0042235 A1    Feb. 15, 2018

Related U.S. Application Data

(63) Continuation of application No. 15/234,621, filed on Aug. 11, 2016, now Pat. No. 9,756,859.

(51) Int. Cl.
| | |
|---|---|
| *A01N 43/80* | (2006.01) |
| *A01N 47/12* | (2006.01) |
| *C09D 5/16* | (2006.01) |
| *A01N 25/04* | (2006.01) |
| *C09D 5/14* | (2006.01) |
| *C09D 7/63* | (2018.01) |
| *A01N 25/30* | (2006.01) |
| *A01N 43/52* | (2006.01) |
| *A01N 47/32* | (2006.01) |
| *C08K 5/00* | (2006.01) |

(52) U.S. Cl.
CPC ............. *A01N 43/80* (2013.01); *A01N 25/04* (2013.01); *A01N 25/30* (2013.01); *A01N 43/52* (2013.01); *A01N 47/12* (2013.01); *A01N 47/32* (2013.01); *C09D 5/14* (2013.01); *C09D 5/1625* (2013.01); *C09D 5/1687* (2013.01); *C09D 7/63* (2018.01); *C08K 5/0058* (2013.01)

(58) Field of Classification Search
CPC ........ A01N 43/80; A01N 47/12; A01N 47/18; A01N 25/04; A01N 25/30; A01N 43/52; A01N 47/32; C09D 5/1625; C09D 5/1687; C09D 5/14; C09D 7/63; C98D 5/1625; C98D 5/1687; C08K 5/0058
See application file for complete search history.

(56) References Cited

U.S. PATENT DOCUMENTS

| | | | | |
|---|---|---|---|---|
| 8,375,494 B2 * | 2/2013 | Hammock | ........... | C11D 3/0031 134/34 |
| 9,756,859 B1 * | 9/2017 | Colon | .................... | A01N 43/80 |
| 2011/0015299 A1 * | 1/2011 | Annis | .................... | C09D 5/025 523/122 |
| 2013/0203825 A1 * | 8/2013 | Premachandran | ..... | A01N 25/04 514/373 |
| 2015/0274595 A1 * | 10/2015 | De Oliveira Filho | ........................ | C04B 40/0039 106/801 |

FOREIGN PATENT DOCUMENTS

WO    WO-2006131147 A1 * 12/2006    ............. A01N 27/00

* cited by examiner

*Primary Examiner* — Anthony J Green
(74) *Attorney, Agent, or Firm* — RatnerPrestia

(57) ABSTRACT

An aqueous dispersion containing BIT and IPBC prepared using nonionic and anionic surfactants exhibits both chemical and physical stability and is suitable for use as a single product which is capable of imparting to a coating composition a high level of resistance against attack by a broad spectrum of organisms, including bacteria, fungi and algae, in both the wet-state and dry film-state.

15 Claims, No Drawings

STABLE AQUEOUS DISPERSIONS OF BIOCIDES

CROSS-REFERENCE TO RELATED APPLICATIONS

This application claims priority of a United States traditional application entitled "STABLE AQUEOUS DISPERSIONS OF BIOCIDES", which is application Ser. No. 15/234,621, filed Aug. 11, 2016 and now U.S. Pat. No. 9,756,859 B1. Application Ser. No. 15/234,621 is hereby incorporated by reference in its entirety.

FIELD OF THE INVENTION

The present invention relates to stable aqueous dispersions of biocides in relatively concentrated form which are useful for formulating compositions such as coating compositions that are resistant to microbiological attack in both the wet state and the dry film state.

DISCUSSION OF THE RELATED ART

The modern era of industrial biocides was ushered in by global regulations banning the use of mercury- and other heavy metal-based biocides. This created an opportunity for the development of a large number of organic compound-based biocides that are safer to use. However, these new types of active ingredients have the disadvantage that they are much more specific and limited in activity. Some are effective against bacteria, some are effective as fungicides and still others are effective as algaecides. Even within each of these organism categories, all of the known organic compound-based biocides have "gaps." That is, they are more effective against certain species of bacteria, fungi or algae than others. As a result, coatings producers have had to use a number of biocide products in order to achieve adequate protection of coating compositions against microbiological attack in both the wet state and the dry film state. At present, coatings producers need to separately purchase and formulate at least two types of biocidal ingredients, a wet state preservative and a dry film preservative. While it has been recognized that in principle it should be possible to combine wet state preservatives and dry film preservatives into a single biocide product having a broad spectrum of activity, the actual formulation of such a product has proven to be challenging. This is because merely combining existing wet state and dry film biocide products results in numerous issues related to both the chemical and physical stability of such combined products. This is especially true for attempts to combine existing BIT-containing wet-state preservative products with IPBC-containing dry-film preservatives. The alkalinity of the BIT preservatives degrades the IPBC over time, making it impractical to offer such combinations for sale since typically end users desire to be able to store biocide ingredients for extended periods prior to using the biocide ingredients in coating compositions and the like. Moreover, due to the water-insolubility of most biocides and the need to avoid the use of organic solvents, biocide products are generally sold in the form of aqueous dispersions having relatively high concentrations of biocide. It has proven to be quite difficult to achieve long term physical stability in such concentrated biocide dispersions, which exhibit a marked propensity to phase separate upon standing. This requires end users to take steps to re-homogenize aqueous dispersions of biocides that have been stored for a period of time, prior to withdrawing portions of such dispersions for use in formulating coating compositions and the like.

Accordingly, there is a need for aqueous dispersions of biocides that are both chemically and physically stable and that, as a single product, provide adequate protection of coating compositions against a wide range of microbiological hazards (i.e., a single product that when formulated into a coating composition simultaneously prevents or retards microbiological growth both when the coating composition is in the wet state as well as when it has been converted into a dry film).

SUMMARY OF THE INVENTION

The present invention provides a single biocide product, in the form of a chemically and physically stable aqueous dispersion, that is capable of imparting a sufficient level of protection to a coating composition, both in the wet state and as a dry film, against a broad range of organism types (algae, bacteria, fungi). Through the use of the inventive biocide compositions described herein, the need to formulate a coating composition using multiple sources of different biocides may be avoided. That is, adequate wet state and dry film state resistance to biological attack of a coating composition may be attained using the inventive aqueous dispersion alone, without the addition of any other biocide-containing ingredient to the coating composition. At the same time, the inventive aqueous dispersion is capable of being stored for extended periods of time at ambient temperatures without significant loss of physical homogeneity or breakdown of the biocide active ingredients.

An aqueous dispersion in accordance with the present invention thus provides the following practical advantages, as compared to the conventional use in the coatings industry of separate wet-state and dry-film preservative packages:

i) Reduced cost to the end user (coatings formulator);

ii) Fewer different inventory items for the end user to purchase, store and maintain;

iii) Operational simplicity, with only one biocide-containing product to be metered into a coating composition rather than several; and iv) Lessened environmental impact, due to the lower energy usage arising from manufacturing, packaging and transporting a single biocide-containing product rather than several.

Various aspects of the invention may be summarized as follows:

Aspect 1: A composition useful for providing resistance to microbiological attack in both a wet state and a dry film state in a single dose, wherein the composition is comprised of, consists essentially of or consists of:

a) water;

b) 1% to 12% by weight 1,2-benzisothiazolin-3-one (BIT);

c) 2% to 50% by weight 3-iodo-2-propynyl butyl carbamate (IPBC), wherein BIT and IPBC are present in amounts effective to provide a weight ratio of BIT:IPBC of from 0.02 to 2;

d) at least one nonionic surfactant;

e) at least one anionic surfactant; and f) at least one thickener/suspending agent, in an amount effective to provide the composition with a viscosity of at least 300 centipoise at 25° C.;

wherein d) and e) are present in an amount effective to provide the composition in the form of a stable aqueous dispersion.

Aspect 2: The composition of Aspect 1, comprising at least two different nonionic surfactants.

Aspect 3: The composition of Aspect 1 or 2, comprising at least one alkoxylated aliphatic or aromatic mono-alcohol.

Aspect 4: The composition of any of Aspects 1-3, comprising at least two different alkoxylated aliphatic mono-alcohols.

Aspect 5: The composition of any of Aspects 1-4, comprising a first alkoxylated aliphatic mono-alcohol and a second alkoxylated aliphatic mono-alcohol each having an aliphatic mono-alcohol segment and an alkoxylated segment, wherein the second alkoxylated aliphatic mono-alcohol differs from the first alkoxylated aliphatic mono-alcohol with respect to at least one of a) chain length of the aliphatic mono-alcohol segment, b) composition of the alkoxylated segment, or c) number of oxyalkylene units in the alkoxylated segment.

Aspect 6: The composition of any of Aspects 1-5, comprising a first alkoxylated aliphatic mono-alcohol which is an ethoxylated C10-C18 aliphatic alcohol containing an average of about 6 to about 15 ethylene oxide units per molecule and a second alkoxylated aliphatic mono-alcohol which is an alkoxylated C2-C8 aliphatic alcohol containing both ethylene oxide and propylene oxide units.

Aspect 7: The composition of Aspect 6, wherein the first alkoxylated aliphatic mono-alcohol is an ethoxylated C12-C16 linear aliphatic alcohol containing an average of about 8 to about 12 ethylene oxide units per molecule.

Aspect 8: The composition of Aspect 6 or 7, wherein the second alkoxylated aliphatic mono-alcohol is an alkoxylated n-butanol containing both ethylene oxide and propylene oxide units and having a block copolymer structure.

Aspect 9: The composition of any of Aspects 1-8, wherein the at least one anionic surfactant includes at least one sulfonate surfactant.

Aspect 10: The composition of any of Aspects 1-9, wherein the at least one anionic surfactant includes at least one alkyl aryl sulfonate.

Aspect 11: The composition of any of Aspects 1-10, wherein the at least one anionic surfactant includes at least one dodecyl benzene sulfonate.

Aspect 12: The composition of any of Aspects 1-11, wherein the at least one thickener/suspending agent includes at least one thickener/suspending agent selected from the group consisting of silicates, polyacrylates, polysaccharides and clays.

Aspect 13: The composition of any of Aspects 1-12, wherein the weight ratio of BIT:IPBC is from 0.5 to 1.8.

Aspect 14: The composition of any of Aspects 1-13, additionally comprising at least one biocide selected from methylbenzimadazole-2-yl carbamate and 3-(3,4-dichlorophenyl)-1,1-dimethylurea.

Aspect 15: The composition of any of Aspects 1-14, wherein the composition is comprised of from about 40 to about 60 weight % water.

Aspect 16: The composition of any of Aspects 1-15, wherein the at least one nonionic surfactant and the at least one anionic surfactant are present in a weight ratio of nonionic surfactant:anionic surfactant of from about 1.5:1 to about 8:1.

Aspect 17: The composition of any of Aspects 1-16, wherein biocides, including BIT and IPBC, the at least one nonionic surfactant and the at least one anionic surfactant are present in a weight ratio of biocides:(nonionic surfactant+anionic surfactant) of from about 6:1 to about 20:1.

Aspect 18: A composition useful for providing resistance to microbiological attack in both a wet state and a dry film state in a single dose, wherein the composition is in the form of a stable aqueous dispersion and is comprised of, consists essentially of or consists of:

a) 45 to 60% by weight water b) 3 to 9% by weight 1,2-benzisothiazolin-3-one (BIT);

c) 2 to 7% by weight 3-iodo-2-propynyl butyl carbamate (IPBC), wherein BIT and IPBC are present in amounts effective to provide a weight ratio of BIT:IPBC of from 0.5 to 1.8;

d) 5 to 20% by weight methylbenzimidazole-2-yl carbamate (BCM);

e) optionally, 3-(3,4-dichlorophenyl)-1,1-dimethylurea;

f) 0.5 to 3% by weight of at least two alkoxylated aliphatic mono-alcohols, including a first alkoxylated aliphatic mono-alcohol which is an ethoxylated C10-C18 aliphatic alcohol containing an average of about 6 to about 15 ethylene oxide units per molecule and a second alkoxylated aliphatic mono-alcohol which is an alkoxylated C2-C8 aliphatic alcohol containing both ethylene oxide and propylene oxide units;

g) 0.2 to 1% by weight of at least one sulfonate surfactant;

h) optionally, up to 1% by weight of at least one defoamer; and i) at least one thickener/suspending agent, in an amount effective to provide the composition with a viscosity of at least 300 cps at 25° C.;

wherein the percentages by weight are based on the total weight of a)-i).

Aspect 19: A coating composition which is resistant to microbiological attack in both a wet state and a dry film state, comprising a composition in accordance with any of Aspects 1-18 and at least one additional coating ingredient.

Aspect 20: A method of making a coating composition which is resistant to microbiological attack in both a wet state and a dry film state, comprising combining one or more coating ingredients with an effective amount of the composition of any of Aspects 1-18 to obtain the coating composition.

"Physically stable", as used herein, means that the aqueous dispersion remains homogeneous and does not phase separate upon sitting for an extended period of time at normal storage conditions. For example, in various embodiments of the invention, the aqueous dispersion may remain homogeneous in appearance, as judged by a human observer, upon sitting (without agitation) at 40° C. for at least one week, at least two weeks, at least one month, at least two months, at least three months, at least four months, at least five months or even at least six months. In such embodiments, the dispersed biocide particles may exhibit no visible settling out or flocculation over at least the stated periods of time.

"Chemically stable", as used herein, means that the active ingredients (biocides) present in the aqueous dispersion do not chemically react or degrade to a significant extent when the aqueous dispersion is stored for an extended period of time under normal storage conditions. For example, in various embodiments of the invention, less than 10% or less than 5% loss of each of the biocides present in the aqueous dispersion takes place upon storage at 40° C. in a sealed container for at least one week, at least two weeks, at least one month, at least two months, at least three months, at least four months, at least five months or even at least six months.

DETAILED DESCRIPTION OF CERTAIN EMBODIMENTS OF THE INVENTION

Water

Water is utilized in the aqueous dispersions of the present invention as a carrier or diluent for the other components of the aqueous dispersions, forming an aqueous phase within which fine particles of the biocides are suspended in the form of an emulsion. Although one or more organic solvents may optionally be present in the aqueous dispersion in addition to water, in particular water-miscible solvents such as alcohols, glycol ethers, esters and the like, it will generally be preferred to minimize the amount of organic solvent or even to eliminate organic solvent altogether. Thus, in various aspects of the invention, the aqueous dispersion contains less than 5%, less than 4%, less than 3%, less than 2%, less than 1%, or less than 0.5% or even 0% by weight, based on the total weight of the aqueous dispersion, of organic solvent. The aqueous dispersion, in one embodiment, is VOC-free (i.e., free of compounds classified as "volatile organic compounds").

Although the pH of the aqueous phase of the aqueous dispersion is not believed to be particularly critical, one or more pH adjusting agents may be included in the aqueous dispersion for the purpose of achieving a desired pH. The pH adjusting agents may be acidic or basic and may also be capable of functioning as buffers. In one aspect of the invention, the aqueous dispersion has a pH of from 3 to 10.

The amount of water may be varied as may be needed or desired in order to provide an aqueous dispersion of suitable stability and biocide concentration. Generally speaking, it will be desirable to minimize the amount of water present in order to provide an aqueous dispersion having as high a concentration of biocides as can be attained while still preserving acceptable rheological properties and dispersion stability. In various embodiments of the invention, the water concentration in the aqueous dispersion may be at least 20%, at least 25%, at least 30%, at least 35%, at least 40% or at least 45% by weight based on the total weight of the aqueous dispersion, while in other embodiments the water concentration in the aqueous dispersion is not more than 80%, not more than 75%, not more than 70%, not more than 65%, not more than 60%, not more than 55%, not more than 50%, not more than 45% or not more than 40% by weight, based on the total weight of the aqueous dispersion. In certain embodiments, the aqueous dispersion is comprised of from 40% to 60% by weight water.

Biocides

The aqueous dispersions of the present invention contain at least two biocides, namely, 1,2-benzisothiazol-3(2H)-one (CAS No. 2634-33-5, at times referred to herein by the acronym "BIT") and 3-iodoprop-2-yn-1-yl butylcarbamate (CAS No. 55406-53-6, at times referred to herein by the acronym "IPBC"). Other commonly used names for BIT include benzisothiazolinone, benzisothiazolin-3-one and benzisothiazolone. IPBC is sometimes alternatively referred to as 3-iodo-2-propynyl N-butylcarbamate, 3-iodo-2-propynyl butyl carbamate or iodocarb. BIT is present in the aqueous dispersion in an amount of from 1% to 12% by weight, while IPBC is present in an amount of from 2% to 50% by weight. In various aspects of the invention, the aqueous dispersion contains 3% to 9% by weight of BIT and 2% to 40% by weight of IPBC. To provide a sufficient degree of both wet state and dry film-state protection to a coating composition based on the aqueous dispersion against biological attack by bacteria, fungi, algae and other organisms, the weight ratio of BIT:IPBC should be controlled to be within the range of from 0.02 to 2, limits included. In one aspect, the BIT:IPBC weight ratio is within the range of 0.5 to 1.8, limits included.

One or more other biocides may be present in the aqueous dispersion compositions of the present invention, in addition to the BIT and the IPBC. In one aspect, the aqueous dispersion additionally comprises methylbenzimidazole-2-yl carbamate ("BCM"). The BCM content of the aqueous dispersion may be, for example, at least 1% by weight and/or not more than 30% by weight, e.g., from 5% to 20% by weight. In a further aspect, the aqueous dispersion additionally comprises 3-(3,4-dichlorphenyl)-1,1-dimethylurea ("Diuron"). The Diuron content of the aqueous dispersion may be, for example, at least 1% by weight and/or not more than 25% by weight, e.g., from 10% to 20% by weight.

The aqueous dispersion may contain both BCM and Diuron, in addition to BIT and IPBC. In various aspects of the invention, the aqueous dispersion contains no biocide other than BIT, IPBC, BCM or Diuron or no more than 10% by weight or no more than 5% by weight (based on the total weight of biocide) of any biocide other than BIT, IPBC, BCM or Diuron. Thus, the aqueous dispersion may have a biocide component consisting of or consisting essentially of BIT and IPBC and optionally one or both of BCM and Diuron.

Other biocides which may be present in the aqueous dispersion include, but are limited to, any of the biocidal compounds known in the art. Supplemental wet-state actives that can be used include, but are not limited to, 5-chloro-2-methyl-2H-isothiazol-3-one/2-methyl-2H-isothiazol-3-one ("CMIT/MIT") and 2-bromo-2-nitropropane-1,3-diol ("Bronopol"). Supplemental algaecides that can be used include, but are not limited to, 2-tert-Butylamino-4-ethyl-amino-6-methylthio-1,3,5-triazin ("Terbutryn") and 3-(4-isopropylphenyl)-1,1-dimethylurea ("Isoproturon").

It will be advantageous for any biocide present in the aqueous dispersion to be in the form of relatively fine particles, for example, particles having a particle size of from 5 to 75 microns. The desired particle size may be attained through the use of conventional techniques such as grinding, milling, sieving and the like.

Surfactants

The aqueous dispersions of the present invention utilize a combination of at least one nonionic surfactant and at least one anionic surfactant. In certain embodiments, the aqueous dispersion is characterized by the absence of any type of surfactant other than nonionic and anionic surfactants, such as cationic or amphoteric (zwitterionic) surfactants. The surfactants function as emulsifiers and help to keep the water-insoluble components of the formulation in the form of a stable dispersion (emulsion) of small particles suspended in an aqueous phase.

In a preferred embodiment, the aqueous dispersion contains at least two different nonionic surfactants. The nonionic surfactants may differ, for example, with respect to the chemical structure (including chain length) of their hydrophobic segment(s), their hydrophilic segment(s), or both their hydrophobic segment(s) and their hydrophilic segment(s). Suitable types of nonionic surfactants include, but are not limited to, polyoxyalkylene glycol alkyl ethers (e.g., polyoxyethylene glycol alkyl ethers, polyoxypropylene alkyl ethers, polyoxyethylene/propylene alkyl ethers), glucoside alkyl ethers, polyoxyalkylene glycol alkylphenol ethers (e.g., polyoxyethylene glycol alkylphenol ethers, polyoxypropylene glycol alkylphenol ethers, polyoxyethylene/propylene glycol alkylphenol ethers), glycerol alkyl esters, polyoxyalkylene glycol sorbitan alkyl esters (e.g., polyoxyethylene glycol sorbitan alkyl esters), sorbitan alkyl esters, cocamide MEA, cocamide DEA, block copolymers of polyethylene glycol and polypropylene glycol (poloxamers), polyalkoxylated tallow amines, alkoxylated fatty acids and the like and combinations thereof.

Particularly advantageous nonionic surfactants include alkoxylated aliphatic mono-alcohols and alkoxylated aromatic mono-alcohols. Such surfactants are typically prepared by reacting one or more alkylene oxides (e.g., ethylene oxide, propylene oxide, mixtures of ethylene oxide and propylene oxide) with one or more mono-alcohols (e.g., aliphatic alcohols, which may be for example linear or branched, primary or secondary, or aromatic alcohols, such as phenols, including alkyl- and aralkyl-substituted phenols). The number of moles of alkylene oxide reacted per mole of the mono-alcohol may be varied as may be desired, but typically is from about 2 to about 50 on average. If more than one type of alkylene oxide is used, the alkylene oxides may be reacted as a mixture (to provide a polyoxyalkylene segment having a random copolymer structure) or sequentially (to provide a polyoxyalkylene segment having a block copolymer structure).

One preferred type of nonionic surfactant for use in the present invention is an alkoxylated aliphatic mono-alcohol which is an ethoxylated C10-C18 aliphatic alcohol (in particular, a linear primary C12-C16 aliphatic alcohol (or mixture of such alcohols) which has been reacted with about 6 to about 15 moles of ethylene oxide per mole of aliphatic alcohol to provide an alkoxylated alcohol containing an average of about 6 to about 15 oxyethylene repeating units per molecule). For example, the alkoxylated aliphatic mono-alcohol may be an ethoxylated C12-C16 linear aliphatic alcohol containing an average of about 8 to about 12 ethylene oxide units per molecule. In particular, ethoxylated tridecanol containing an average of about 10 ethylene oxide units is suitable for use in the present invention.

Another preferred type of nonionic surfactant for use in the present invention is an alkoxylated C2-C8 aliphatic alcohol containing both ethylene oxide and propylene oxide units. The C2-C8 aliphatic alcohol may be n-butanol, for example. The ethylene oxide and propylene units may be arranged in a block manner (e.g., the surfactant may contain a polyoxyethylene block and a polyoxypropylene block).

Also suitable for use as nonionic surfactants are alkoxylated phenols, in particular ethoxylated phenols wherein the phenol may be substituted with one or more alkyl groups (in particular, long chain alkyl groups such as nonyl or dodecyl groups or aralkyl groups, such as in tristyrylphenol).

Suitable anionic surfactants include, but are not limited to, surfactants containing anionic functional groups at their head, such as sulfate groups, sulfonate groups, phosphate groups, and carboxylate groups. The cationic counterion to the anionic functional group may be, for example, an alkali metal (e.g., Na, K) or an amine (ammonium) cation such as a quaternary ammonium. Useful types of anionic surfactants which may be employed in the aqueous dispersions of the present invention include, but are not limited to, alkyl sulfates, alkyl ether sulfates, sulfated alkanolamides, glyceride sulfates, alkyl aryl sulfonates (including straight-chain alkylbenzenesulfonates, branched alkylbenzenesulfonates, alkylnaphthalenesulfonates), alpha olefin sulfonates, lignosulfonates, sulfo-carboxylic compounds (e.g., sodium lauryl sulfoacetate, sulfosuccinates (including dialkylsulfosuccinates), sulfosuccinamates, organo phosphored surfactants, sacrosides, hydroxyalkanesulfonates, alkanesulfonates, alkylphenoxy polyoxyethylene propyl sulfonates, salts of polyoxyethylene alkylsulfophenyl ethers, sodium N-methyl-N-oleyltaurates, monoamide disodium N-alkyl sulfosuccinates, petroleum sulfonates, sulfated castor oil, sulfated tallow oil, salts of sulfuric esters of aliphatic alkylesters, salts of alkylsulfuric esters, salts of alkylsulfuric esters, sulfuric esters of polyoxyethylenealkylethers, salts of sulfuric esters of aliphatic monoglycerides, sodium salt of the monosulfated monoglyceride of hydrogenated coconut oil fatty acids, salts of sulfuric esters of polyoxyethylene alkylphenylethers, salts of alkylphosphoric esters, salts of phosphoric esters of polyoxyethylenealkylethers, salts of phosphoric esters of polyoxyethylenealkylphenylethers, partially saponified compounds of styrene-maleic anhydride copolymers, partially saponified compounds of olefin-maleic anhydride copolymers, naphthalenesulfonate-formalin condensates, higher alkyl sulfoacetates, and higher fatty acid esters of 1,2-dihydroxy propane sulfonate and combinations thereof. Particularly preferred among these anionic surfactants are sulfonate surfactants, in particular salts of alkyl aryl sulfonates, especially salts of C8-C18 alkyl benzene sulfonates such as salts of dodecylbenzene sulfonate, and combinations thereof.

A total amount of surfactant is utilized in the composition which is effective, in combination with the thickener(s)/suspending agent(s) also present in the composition, to provide a physically stable aqueous dispersion. The amount of surfactant needed to achieve a physically stable dispersion will depend on a number of factors, including, for instance, the types and amounts of biocides and thickeners/suspending agents present and well as the types of surfactants utilized. Typically, however, an amount of surfactant is used which is sufficient to provide a weight ratio of biocide:surfactant within the range of from about 5:1 to about 50:1 or from about 6:1 to about 20:1.

Thickeners/Suspending Agents

The aqueous dispersions of the present invention additionally include at least one substance capable of functioning as a thickener or suspending agent such that, in cooperation with the surfactant component, the aqueous dispersion is rendered physically stable. In particular, the type(s) and amount(s) of thickener/suspending agent are selected such that at 25° C. the resulting aqueous dispersion has a viscosity of at least 300 cps. In other embodiments, the viscosity of the aqueous dispersion at 25° C. is at least 400 cps or at least 500 cps. Generally speaking, however, it will be desirable for the viscosity of the aqueous dispersion to not be increased to the point where it becomes difficult to transfer or handle the aqueous dispersion by means of pumping. Viscosity is measured using a Brookfield viscometer (spindle #5, 100 rpm).

Suitable thickeners/suspending agents include, without limitation, clays (including natural clays and organo-modified clays), silicates (e.g., silicas such as modified silicas and fumed silicas), polysaccharides (e.g., gums such as xanthan gum, cellulosic polymers), polyacrylates, and the like and combinations thereof.

Optional Additional Ingredients

One or more other components, in addition to those mentioned above, may additionally be present in the aqueous dispersions of the present invention. In certain embodiments, however, the aqueous dispersion consists essentially of or consists of only the aforementioned components, except that one or more defoamers may optionally be present in such embodiments.

Optional additional components include, but are not limited to, defoamers (antifoams, e.g., silicone-based defoamers, mineral oil-based defoamers, hydrophobic silica-based defoamers), sequestering/chelating agents, pH adjusting agents, fillers, coloring agents, antifreezing agents, corrosion inhibitors (anti-corrosion additives), ultraviolet light stabilizers, antioxidants, co-solvents, scale inhibitors, preservative, and the like.

Methods of Making

Aqueous dispersions in accordance with the present invention may be prepared by adaptation of any of the techniques known in the art for creating dispersions of water-insoluble substances in water using surfactants (emulsifiers) and thickeners/suspending agents. For example, and as further illustrated by the working examples included herein, a suitably sized mixing vessel may be charged with water, followed by the surfactants desired to be included in the aqueous dispersion. While agitating the surfactant/water mixture, the biocides and a portion of the thickeners/suspending agents are added. Mixing at high speed and/or high shear may be continued until a homogeneous emulsion having the desired particle size (typically 5 to 75 microns) is obtained. The mixture may be heated to a temperature somewhat above room temperature during this step. The remaining thickeners/suspending agents may then be added and the mixture agitated until homogeneous once again. The mixture may be cooled to room temperature prior to the final addition of thickeners/suspending agents. The aqueous dispersion may then be transferred by pumping or other means to one or more suitable storage containers such as tanks, drums or totes.

End Uses

Aqueous dispersions in accordance with the present invention are useful for imparting resistance to microorganism growth, including bacterial, fungal and algae growth, in a wide variety of products, in particular water-based products. As the aqueous dispersions are typically prepared containing relatively high concentrations of active ingredients (i.e., biocides), they generally find use as concentrates which are combined, in relatively small quantities, with one or more other ingredients in order to formulate a final product suitable for use for its intended purpose (such as a coating composition, for example, wherein the other ingredients may include pigment(s), polymeric resin(s) (e.g., latex resins), a carrier vehicle such as water and so forth). In one embodiment of the invention, the aqueous dispersion is dosed into a coating composition, in particular a water-based coating composition such as a latex paint, in an amount representing from 0.2 to 2% by weight of the coating composition.

The aqueous dispersions of the present invention may, for instance, be employed any of the following types of products: wood preservatives, paints, lazures, stains, plasters, EFIS (Exterior Finishing Insulation System, sometimes also referred to as Exterior Insulation Finishing System), mildewicides, adhesives, textiles, leather and hide treatment, non-woven fabrics, building materials, stucco, concrete, caulks, sealants, joint compounds, and any other application in which the inhibition or prevention of the growth of undesired microorganisms is desired in both the wet-state and the dry-film state.

Within this specification, embodiments have been described in a way which enables a clear and concise specification to be written, but it is intended and will be appreciated that embodiments may be variously combined or separated without departing from the invention. For example, it will be appreciated that all preferred features described herein are applicable to all aspects of the invention described herein.

In some embodiments, the invention herein can be construed as excluding any element or process step that does not materially affect the basic and novel characteristics of the composition or process. Additionally, in some embodiments, the invention can be construed as excluding any element or process step not specified herein.

Although the invention is illustrated and described herein with reference to specific embodiments, the invention is not intended to be limited to the details shown. Rather, various modifications may be made in the details within the scope and range of equivalents of the claims and without departing from the invention.

EXAMPLES

Example 1

This Example demonstrates the preparation of a stable aqueous dispersion in accordance with the present invention which is suitable for use in an interior paint product to provide simultaneous wet-state and dry film-state protection against biological attack.

To an appropriate size mixing vessel equipped with a high speed mixer, charge 51 parts water and start mixing at low speed. Charge the following ingredients in succession: 0.6 parts by weight dodecylbenzene sulfonic acid isopropylamine salt, 0.4 parts by weight alkoxylated alcohol surfactant A (ethoxylated tridecanol containing an average of about 10 ethylene oxide units per molecule), and 1 part by weight alkoxylated alcohol surfactant B (n-butanol alkoxylated with propylene oxide and ethylene oxide in a block manner). While gradually increasing agitation as the mixture thickens, add the following ingredients: 7.2 parts by weight 1,2-benzisothiazolin-3-one (BIT, 85%), 15 parts by weight methylbenzimdazole-2-yl carbamate (BCM, technical grade), 15.3 parts by weight natural clay (thickener), 1 part by weight modified silica (suspending agent), 5.4 parts by weight 3-iodo-2-propynyl butyl carbamate (IPBC), and 0.2 parts by weight defoamer. While maintaining a temperature at or below 40° C., mix at high speed until a homogeneous emulsion with a desired particle size, typically 5 to 75 microns, is reached. Cool to room temperature, then add 0.3 parts by weight xanthan gum (thickener) and 0.4 parts by weight of a product containing 9.5% by weight BIT and 90.5% by weight inert ingredients. Stir for 30 minutes until homogeneous. The resulting creamy white emulsion was analyzed and found to contain 4.5% by weight IPBC, 14.6% by weight BCM, and 6.4% by weight BIT and to have a viscosity at 25° C. of 642 cps. After holding for three months at 40° C., the creamy white emulsion was found to contain 4.2% by weight IPBC, 14.3% by weight BCM, and 6.2% by weight BIT. The product obtained remained a homogeneous creamy white emulsion after holding for three months at 40° C.

The ability of the product thus prepared to provide bacterial resistance to a coating composition was demonstrated by stirring a portion of the aqueous dispersion of Example 1 into a standard acrylic paint containing no microbicide. A 50-gram aliquot of each sample was inoculated with 0.5 mL of a mixed bacterial culture containing *Alcaligenes faecalis* (ATCC #25094), *Enterobacter aerogenes* (ATCC #13048), *Escherichia coli* (ATCC #11229), and *Pseudomonas aeruginosa* (ATCC #10145). The resulting aliquot was streaked on Petri dishes of TGEA at intervals of 24 hours, 48 hours, and 7 days. To obtain a second week of data, the same samples were re-inoculated with the same mixed culture and retested. The Petri dishes were evaluated for extent of bacterial growth using a subjective scale from 0 to 4, where 0 is completely free of growth and 4 is completely overgrown. The results obtained are shown in Table 1.

TABLE 1

| | Bacterial Resistance | | | | | | Mildew Resistance | | | |
|---|---|---|---|---|---|---|---|---|---|---|
| | First Inoculation | | | Second Inoculation | | | A. niger | A. pullans | T. viride | P. fellutanum |
| | 24 hr | 48 hr | 7 days | 24 hr | 48 hr | 7 da | 4 wk | 4 wk | 4 wk | 4 wk |
| Blank | 4 | 4 | 4 | 4 | 4 | 4 | 4 | 2 | 3 | 3 |
| 0.2% Example 1 | 1 | 0 | 0 | 2 | 0 | 0 | 1 | 1 | 1 | 1 |
| 0.3% Example 1 | 0 | 0 | 0 | 1 | 0 | 0 | 1 | 1 | 1 | 1 |

Mildew resistance was demonstrated on the same spiked paint above. The paint was applied over Leneta charts and cured for 7 days. The squares were placed on sterile 2% Malt Agar petri plates. Spore suspensions of the four fungal species were made from four-week-old cultures grown on Malt Agar. Each test organism was tested separately. One mL of an individual fungal spore suspension was distributed over the surface of each sample. Duplicate plates of each sample were prepared. The petri plates containing the test samples were incubated for four weeks at 80° F. and 70% relative humidity. Each sample was evaluated for extent of fungal growth at four weeks using a subjective scale from 1 to 4 where 1 is completely free of growth and 4 is completely overgrown. Test organisms were *Aspergillus niger* (ATCC #1015), *Aureobasidium pullulans* (ATCC #9348), *Penicillium fellutanum* (ATCC #10443), and *Trichoderma viride* (ATCC #20476). The ratings observed are shown in Table 1.

Example 2

This Example demonstrates the preparation of a stable aqueous dispersion in accordance with the present invention which is suitable for use in an exterior paint product to provide simultaneous wet-state and dry film-state protection against biological attack.

To an appropriate size mixing vessel equipped with a high speed mixer, charge 53.6 parts water and start mixing at low speed. Charge the following ingredients in succession: 0.6 parts by weight dodecylbenzene sulfonic acid isopropylamine salt, 0.4 parts by weight alkoxylated alcohol surfactant A (ethoxylated tridecanol containing an average of about 10 ethylene oxide units per molecule), 1 part by weight alkoxylated alcohol surfactant B (n-butanol alkoxylated with propylene oxide and ethylene oxide in a block manner), and 2 parts by weight ethoxylated tristyrylphenol (containing an average of about 16 moles ethylene oxide per mole of tristyrylphenol). While gradually increasing agitation as the mixture thickens, add the following ingredients: 4.3 parts by weight 1,2-benzisothialin-3-one (BIT, 85%), 15.5 parts by weight 3-(3,4-dichlorphenyl)-1,1-dimethylurea (Diuron), 9.3 parts by weight methylbenzimidazole-2-yl carbamate (BCM, technical grade), 10.2 parts by weight natural clay (thickener), 1 part by weight modified silica, 3.4 parts by weight 3-ido-2-propynyl butyl carbamate (IPBC), and 0.6 parts by weight defoamer. While maintaining a temperature at or below 40°, mix at high speed for 2 hours or until a homogeneous emulsion with a desired particle size, typically 5 to 75 microns, is reached. Cool to room temperature, then add 0.3 parts by weight xanthan gum (thickener) and 0.4 parts by weight of a product containing 9.5% by weight BIT and 90.5% by weight inert ingredients. Stir for 30 minutes until homogeneous. The resulting creamy white emulsion was analyzed and found to contain 3.7% by weight IPBC, 9.1% by weight BCM, 6.5% by weight BIT, and 15.4% by weight Diuron and to have a viscosity at 25° C. of 642 cps.

The product obtained remained a homogeneous creamy white emulsion after holding for one month at 40° C. At this time, the creamy white emulsion was found to contain 3.4% IPBC, 8.8% BCM, 3.4% BIT and 15.2% by weight Diuron.

The aqueous dispersion obtained was subjected to the same test protocol as described in Example 1. The results of the testing are shown in Table 2. Since the aqueous dispersion additionally contained an algaecide, it was also evaluated for algae resistance.

Algae resistance was demonstrated on the same spiked paint above. One coat of each sample was applied to both sides of Whatman #2 filter paper in duplicate and air dried for 72 hours. A 0.35 ml suspension of algae was spread over the plate with a "Drigalski" spatula. Two 1 inch squares were cut from each specimen and placed on Proteose agar plates. One-hundred (100) µl of algae suspension was placed on top of each filter paper square. The petri dishes were then incubated for two weeks at 15 degrees C., 52% RH and 4000-lux light. The samples were evaluated for extent of algae growth at four weeks using a subjective scale from 1 to 4, where 1 is completely free of growth and 4 is completely overgrown. Test Organisms were *Chlorella vulgaris* var *viridis* (ATCC #16487), *Chlorella* sp. (Troy isolate), and *Stichococcus bacillaris* (BIUC #K-150). Ratings are shown in Table 2.

TABLE 2

| | Bacterial Resistance | | | | | | Mildew Resistance | | | | Algae Resistance *Chlorella vulgaris varviridis* + *Chlorella* sp. + *Stichococcus bacillaris* |
| | First Inoculation | | | Second Inoculation | | | *A. niger* | *A. pullans* | *T. viride* | *P. fellutanum* | |
| | 24 hr | 48 hr | 7 da | 24 hr | 48 hr | 7 da | 4 Wk | 4 Wk | 4 Wk | 4 Wk | 4 Wk |
|---|---|---|---|---|---|---|---|---|---|---|---|
| Blank | 4 | 4 | 4 | 4 | 4 | 4 | 4 | 2 | 3 | 3 | 2 |
| 0.2% Example 2 | 0 | 0 | 0 | 1 | 0 | 0 | 1 | 1 | 1 | 1 | 0 |

The following examples (Examples 3 and 4) illustrate that it is not possible to blend conventional BIT-containing wet-state solutions and combine them with existing IPBC-containing dry-film products and obtain a chemically or physically stable biocidal product.

Example 3

To an appropriate size mixing vessel equipped with a high speed mixer, charge 2 parts by weight Polyphase® 678 (a water-based dispersion of IPBC and BCM, sold by Troy Corporation) and 3 parts by weight Mergal® B10K (a ready-to-use solution containing 9.5% by weight BIT, sold by Troy Corporation). The resulting creamy white emulsion was analyzed and found to contain 1.97% by weight IPBC, 5.9% by weight BCM and 6% by weight BIT. After holding at 3 months at 40° C., the mixture was again analyzed and found to contain 0.55% IPBC, 6.2% BCM and 4.8% BIT (i.e., significant loss of IPBC and BIT had occurred). Upon standing at room temperature for two weeks, the emulsion broke, forming two layers.

Example 4

To an appropriate size mixing vessel equipped with a high speed mixer, charge 2 parts by weight Polyphase® 663 (a water-based product containing 9% by weight BCM, 3% by weight IPBC and 15% by weight Diuron), and 3 parts by weight Mergal® B10K (a ready-to-use solution containing 9.5% by weight BIT, sold by Troy Corporation). Upon standing at room temperature for two weeks, the emulsion broke to form two layers.

The following examples (Examples 5-7) illustrate that it is not possible to even blend BIT-containing wet-state dispersions (which avoids the alkalinity that destroys IPBC) and combine them with existing IPBC-containing dry-film products and obtain a physically stable biocidal product.

Example 5

A mixture of 11.3 grams Mergal® 753 (an aqueous dispersion product containing 44.9% by weight BIT sold by Troy Corporation), 38 grams Polyphase® 678 (a water-based dispersion of IPBC, sold by Troy Corporation), and 50.7 grams deionized water were added to a beaker and mechanically stirred for 15 minutes. When mechanical stirring stopped, the resulting milky white dispersion separated into two layers. This demonstrates that even the simple blending of existing wet-state and dry-film dispersion products does not result in a physically stable product.

Example 6

A mixture of 10 grams Mergal® 753 (an aqueous dispersion product containing 44.9% by weight BIT sold by Troy Corporation), 67.4 grams Polyphase® 678 (a water-based dispersion of IPBC, sold by Troy Corporation), and 20.6 grams deionized water were added to a beaker and mechanically stirred for 15 minutes. When mechanical stirring stopped, the resulting milky white dispersion separated into two layers Example 7

A mixture of 11.3 grams Mergal® 753 (an aqueous dispersion product containing 44.9% by weight BIT sold by Troy Corporation), 38 grams Polyphase® 663 (a water-based product containing 9% by weight BCM, 3% by weight IPBC and 15% by weight Diuron), and 50.7 grams deionized water were added to a beaker and mechanically stirred for 15 minutes. When mechanical stirring was stopped, the resulting milky white dispersion separated into two layers.

Example 8

A stable aqueous dispersion in accordance with the present invention which is suitable for use as a concentrate in the formulation of an exterior paint may be prepared using the procedures described in Examples 1 and 2 and the components listed in Table 2.

TABLE 2

| Component | Weight Percent | Function |
|---|---|---|
| Dodecylbenzene Sulfonic Acid Isopropyl amine Salt | 0.6 | Surfactant (Emulsifier) |
| Alkoxylated Alcohol Surfactant A[1] | 0.4 | Surfactant (Emulsifier) |
| Modified Silica | 1 | Thickener/Suspending Agent |
| Alkoxylated Alcohol Surfactant B[2] | 1 | Surfactant (Emulsifier) |
| Polyacrylate | 2 | Thickener/Suspending Agent |
| Natural Clay | 10.2 | Thickener/Suspending Agent |

TABLE 2-continued

| Component | Weight Percent | Function |
|---|---|---|
| Diuron | 15.5 | Active Ingredient (Biocide) |
| Xanthan Gum | 0.3 | Thickener/Suspending Agent |
| Defoamer | 0.6 | Defoamer |
| Mergal ® (4) K10N[3] | 0.4 | Active Ingredient (Biocide) |
| 1,2-Benzisothiazolin-3-one (BIT, 85%) | 4.3 | Active Ingredient (Biocide) |
| Water | 51 | Diluent |
| BCM | 9.3 | Active Ingredient (Biocide) |
| IPBC | 3.4 | Active Ingredient (Biocide) |

[1] ethoxylated tridecanol containing an average of about 10 ethylene oxide units per molecule
[2] n-butanol alkoxylated with propylene oxide and ethylene oxide in a block manner
[3] a ready-to-use solution containing 9.5% by weight BIT, sold by Troy Corporation Example 9

A stable aqueous dispersion in accordance with the present invention which is suitable for use as a concentrate in the formulation of an interior paint may be prepared using the procedures described in Examples 1 and 2 and the components listed in Table 3.

TABLE 3

| Component | Weight Percent | Function |
|---|---|---|
| Dodecylbenzene Sulfonic Acid Isopropylamine Salt | 0.6 | Surfactant (Emulsifier) |
| Alkoxylated Alcohol Surfactant A[1] | 0.4 | Surfactant (Emulsifier) |
| Modified Silica | 1 | Thickener/Suspending Agent |
| Alkoxylated Alcohol Surfactant B[2] | 1 | Surfactant (Emulsifier) |
| Natural Clay | 15.3 | Thickener/Suspending Agent |
| Xanthan Gum | 0.3 | Thickener/Suspending Agent |
| Defoamer | 0.2 | Defoamer |
| 1,2-Benzisothiazolin-3-one (BIT, 85%) | 7.2 | Active Ingredient (Biocide) |
| Water | 53.6 | Diluent |
| BCM | 15 | Active Ingredient (Biocide) |
| IPBC | 5.4 | Active Ingredient (Biocide) |

Example 10

A stable aqueous dispersion in accordance with the present application may be prepared using the following procedure. To an appropriate size mixing vessel equipped with a high speed mixer, charge 41.6 parts by weight water and start mixing at low speed. Charge 1 part by weight of a nonionic alkoxylated alcohol surfactant which is n-butanol alkoxylated with propylene oxide and ethylene oxide in a block manner and 0.6 part by weight of an anionic surfactant which is the isopropyl amine salt of dodecylbenzene sulfonate. While gradually increasing agitation as the mixture thickens, add the following ingredients: 7.2 parts by weight BIT (85%), 0.5 part by weight fumed silica, 8.7 parts by weight natural clay (thickener), 40 parts by weight IPBC, 0.1 parts by weight defoamer, and 0.3 parts xanthan gum (thickener). Stir for 30 minutes until homogeneous.

What is claimed is:

1. A composition useful for providing resistance to microbiological attack in both a wet state and a dry film state in a single dose, wherein the composition is comprised of:
    a) water;
    b) 1% to 12% by weight 1,2-benzisothiazolin-3-one (BIT);
    c) 2% to 50% by weight 3-iodo-2-propynyl butyl carbamate (IPBC);
    d) a nonionic surfactant which includes an ethoxylated tristyrylphenol containing about 16 moles of ethylene oxide per mole of phenol;
    e) an anionic surfactant which includes an alkylbenzene sulfonate; and
    f) at least one thickener/suspending agent, in an amount effective to provide the composition with a viscosity of at least 300 centipoise at 25 degrees C.;
    wherein BIT and IPBC are present in amounts effective to provide a weight ratio of BIT to IPBC in the range of 0.02 to 2; and
    wherein d) and e) are present in an amount effective to provide the composition in the form of a stable aqueous dispersion.

2. The composition of claim 1, in which the alkylbenzene sulfonate is dodecylbenzene sulfonate.

3. The composition of claim 1 in which the non-ionic surfactant additionally includes a first alkoxylated aliphatic mono-alcohol and a second alkoxylated aliphatic mono-alcohol, each having an aliphatic mono-alcohol segment and an alkoxylated segment, wherein the second alkoxylated aliphatic mono-alcohol differs from the first alkoxylated aliphatic mono-alcohol with respect to at least one of a) chain length of the aliphatic mono-alcohol segment, b) composition of the alkoxylated segment, or c) number of oxyalkylene units in the alkoxylated segment.

4. The composition of claim 3, in which the first alkoxylated aliphatic mono-alcohol is an ethoxylated C10-C18 aliphatic alcohol containing an average of about 6 to about 15 ethylene oxide units per molecule and the second alkoxylated aliphatic mono-alcohol is an alkoxylated C2-C8 aliphatic alcohol containing both ethylene oxide and propylene oxide units.

5. The composition of claim 4, in which the first alkoxylated aliphatic mono-alcohol is an ethoxylated C12-C16 linear aliphatic alcohol containing an average of about 8 to about 12 ethylene oxide units per molecule.

6. The composition of claim 4, in which the second alkoxylated aliphatic mono-alcohol is an alkoxylated n-butanol containing both ethylene oxide and propylene oxide units and having a block copolymer structure.

7. The composition of claim 1, in which the at least one thickener/suspending agent includes a thickener/suspending agent selected from the group consisting of silicates, polyacrylates, polysaccharides and clays.

8. The composition of claim 1, in which the weight ratio of BIT:IPBC is in the range of 0.5 to 1.8.

9. The composition of claim 1, which includes a biocide selected from the group consisting of methylbenzimadazole-2-yl carbamate and 3-(3,4-dichlorophenyl)-1,1-dimethylurea and mixtures thereof.

10. The composition of claim 1, which includes about 40 to about 60 weight % water.

11. The composition of claim 1, in which the nonionic surfactant and the anionic surfactant are present in a weight ratio of nonionic surfactant to anionic surfactant in the range of about 1.5:1 to about 8:1.

12. The composition of claim 1, in which biocides, including BIT and IPBC, and the nonionic surfactant and the anionic surfactant are present in a weight ratio of (biocides):(nonionic surfactant+anionic surfactant) in the range of about 6:1 to about 20:1.

13. A coating composition which is resistant to microbiological attack in both a wet state and a dry film state, comprising a composition in accordance with claim 1 and at least one additional coating ingredient.

14. A method of making a coating composition, comprising combining one or more coating ingredients with an amount of the composition of claim 1 to obtain a coating composition which is resistant to microbiological attack in both a wet state and a dry film state.

15. A composition useful for providing resistance to microbiological attack in both a wet state and a dry film state in a single dose, wherein the composition is in the form of a stable aqueous dispersion and comprises:
 a) 45 to 60% by weight water;
 b) 3 to 9% by weight 1,2-benzisothiazolin-3-one (BIT); and
 c) 2 to 7% by weight 3-iodo-2-propynyl butyl carbamate (IPBC), wherein BIT and IPBC are present in amounts effective to provide a weight ratio of BIT:IPBC in the range of 0.5 to 1.8;
 d) 5 to 20% by weight methylbenzimidazole-2-yl carbamate (BCM) or 3-(3,4-dichlorophenyl)-1,1-dimethylurea;
 e) 0.5 to 3% by weight at least two alkoxylated aliphatic mono-alcohols, including a first alkoxylated aliphatic mono-alcohol which is an ethoxylated C10-C18 aliphatic alcohol containing an average of about 6 to about 15 ethylene oxide units per molecule and a second alkoxylated aliphatic mono-alcohol which is an alkoxylated C2-C8 aliphatic alcohol containing both ethylene oxide and propylene oxide units;
 f) 0.2 to 1% by weight dodecylbenzene sulfonate surfactant; and
 g) at least one thickener/suspending agent, in an amount effective to provide the composition with a viscosity of at least 300 cps at 25 degrees C.; wherein the percentages by weight are based on the total weight of a) through g).

* * * * *

UNITED STATES PATENT AND TRADEMARK OFFICE
CERTIFICATE OF CORRECTION

PATENT NO. : 10,149,475 B2
APPLICATION NO. : 15/674474
DATED : December 11, 2018
INVENTOR(S) : Ismael Colon et al.

Page 1 of 1

It is certified that error appears in the above-identified patent and that said Letters Patent is hereby corrected as shown below:

In the Specification

At Column 12, Line 27, "6.5% by weight BIT" should be corrected to read --3.6% by weight BIT--

Signed and Sealed this
Twenty-eighth Day of January, 2020

Andrei Iancu
*Director of the United States Patent and Trademark Office*